(12) United States Patent
Sugano

(10) Patent No.: US 9,746,318 B2
(45) Date of Patent: Aug. 29, 2017

(54) IMAGING APPARATUS AND IMAGING METHOD

(71) Applicant: Mitsubishi Electric Engineering Company, Limited, Tokyo (JP)

(72) Inventor: Tetsuo Sugano, Tokyo (JP)

(73) Assignee: Mitsubishi Electric Engineering Company, Limited, Tokyo (JP)

( * ) Notice: Subject to any disclaimer, the term of this patent is extended or adjusted under 35 U.S.C. 154(b) by 185 days.

(21) Appl. No.: 14/402,947

(22) PCT Filed: Mar. 5, 2013

(86) PCT No.: PCT/JP2013/055962
§ 371 (c)(1),
(2) Date: Nov. 21, 2014

(87) PCT Pub. No.: WO2013/175827
PCT Pub. Date: Nov. 28, 2013

(65) Prior Publication Data
US 2015/0145987 A1 May 28, 2015

(30) Foreign Application Priority Data
May 24, 2012 (JP) ................................. 2012-118343

(51) Int. Cl.
*H04N 7/18* (2006.01)
*H04N 13/00* (2006.01)
(Continued)

(52) U.S. Cl.
CPC ............ *G01B 11/25* (2013.01); *A61B 5/0064* (2013.01); *A61B 5/0071* (2013.01); *A61B 5/1077* (2013.01); *F04C 2270/041* (2013.01)

(58) Field of Classification Search
USPC ....... 348/135, 61, 64, 65, 42, 45, 51, 66, 67
See application file for complete search history.

(56) References Cited

U.S. PATENT DOCUMENTS

| | | | | |
|---|---|---|---|---|
| 6,987,531 B2* | 1/2006 | Kamon | ............ | H04N 13/0207 348/135 |
| 8,731,367 B2* | 5/2014 | Sakaguchi | ............. | A61B 6/461 348/45 |
| 2008/0266391 A1* | 10/2008 | Lee | .................... | G01B 11/0608 348/135 |

FOREIGN PATENT DOCUMENTS

CN 102165762 A 8/2011
CN 1022319059 A 1/2012
(Continued)

OTHER PUBLICATIONS

International Search Report issued in International Application No. PCT/JP2013/055962 on Apr. 23, 2013, 2 pages.
(Continued)

*Primary Examiner* — Daquan Zhao
(74) *Attorney, Agent, or Firm* — Rothwell, Figg, Ernst & Manbeck, P.C.

(57) ABSTRACT

An imaging apparatus includes: a light source section (2, 40) including a light source having a wavelength of a plurality of bands; an imaging section (15) configured to convert measurement light source light images of the plurality of bands from the light source section into a plurality of electrical measurement imaging signals, the measurement light source light images being reflected from a surface and an inside of the subject; a calculation section (13, 16, 19) configured to measure a shape of the surface and a shape of the inside in the subject based on the plurality of electrical measurement imaging signals obtained through the conversion in the imaging section; and a composition processing section (19) configured to composition-process the shape of the surface and the shape of the inside measured by the calculation section to create two-dimensional image data or three-dimensional image data about the subject.

10 Claims, 12 Drawing Sheets

(51) Int. Cl.
*H04N 13/04* (2006.01)
*G01B 11/25* (2006.01)
*A61B 5/00* (2006.01)
*A61B 1/04* (2006.01)
*A61B 5/107* (2006.01)

(56) References Cited

FOREIGN PATENT DOCUMENTS

| | | | |
|---|---|---|---|
| JP | 2006-098340 A | 4/2006 |
| JP | 2006-130201 A | 5/2006 |
| JP | 2006-177781 A | 7/2006 |
| JP | 2010-218 A | 1/2010 |
| JP | 2010-220669 A | 10/2010 |

OTHER PUBLICATIONS

Chinese Office Action dated May 4, 2016, CN Application No. 201380025798.9, 8 pages.

\* cited by examiner

PATTERN A   PATTERN B   PATTERN C

| SPACE CODE | 1 | 1 | 1 | 1 | 0 | 0 | 0 | 0 | = A |
|---|---|---|---|---|---|---|---|---|---|
|  | 1 | 1 | 0 | 0 | 1 | 1 | 0 | 0 | = B |
|  | 1 | 0 | 1 | 0 | 1 | 0 | 1 | 0 | = C |

| DECIMAL NUMBER REPRESENTATION | 7 | 6 | 5 | 4 | 3 | 2 | 1 | 0 |

IMAGING APPARATUS AND IMAGING METHOD

CROSS REFERENCE TO RELATED APPLICATIONS

This application is a 35 U.S.C. §371 National Phase Entry Application from PCT/JP2013/055962, filed Mar. 5, 2013, and designating the United States, which claims priority under 35 U.S.C. §119 to Japanese Patent Application No. 2012-118343 filed May 24, 2012, which is incorporated herein by reference in its entirety.

TECHNICAL FIELD

The present invention pertains to a field of a medical camera which is utilized in a phase of a surgical operation, and relates to an imaging method and apparatus for carrying out measurement of a three-dimensional image of an object to be imaged.

BACKGROUND ART

In a three-dimensional measurement instrument used in a medical treatment such as a surgical operation, there is a technique for measuring a three-dimensional position of a specific site of the human body based on imaging information acquired from a plurality of cameras by using ultraviolet light, visible light, or near-infrared light (for example, refer to Patent Literature 1).

CITATION LIST

Patent Literature

[PTL 1] JP 3152810 B2

SUMMARY OF INVENTION

Technical Problem

However, the related art involves the following problems.

A technique disclosed in Patent Literature 1 is suitable for the measurement of the specific site by utilizing a special probe. For this reason, the technique disclosed in Patent Literature 1 is unsuitable for measuring some extent of a range of an associated site for the surgical operation. In addition, the three-dimensional information as the measurement result has been mere superficial information in a range seen with the naked eye.

For example, in the case of such a situation that vascular system sites such as a lymph node, a vein, and an artery are present right under a site intended to be deleted in the surgical operation, and hence those sites should not be damaged by a scalpel or the like in a phase of the surgical operation, the surgical operation relies on the operator's experience and intuition. Hence, in that sense, the risk usually exists. In a word, there has been a problem in that only the superficial information in the range of being seen with the naked eye is hard to use in the actual surgical operation.

The present invention has been made in order to solve the problem as described above, and it is therefore an object of the present invention to obtain an imaging apparatus and an imaging method each of which is capable of providing image information for exactly confirming and grasping shapes and states of a surface and an inside of a subject as an object of a surgical operation.

Solution to Problem

According to one embodiment of the present invention, there is provided an imaging apparatus, including: a light source section including a light source having a wavelength of a plurality of bands, the light source section being used to measure a shape of a subject as an object of a surgical operation; an imaging section configured to convert measurement light source light images of the plurality of bands from the light source section into a plurality of electrical measurement imaging signals, the measurement light source light images being reflected from a surface and an inside of the subject; a calculation section configured to measure a shape of the surface and a shape of the inside in the subject based on the plurality of electrical measurement imaging signals obtained through the conversion in the imaging section; and a composition processing section configured to composition-process the shape of the surface and the shape of the inside measured by the calculation section to create one of two-dimensional image data and three-dimensional image data about the subject.

Further, according to one embodiment of the present invention, there is provided an imaging method, including: a light source step of carrying out irradiation from a light source having a wavelength of a plurality of bands to a subject as an object of a surgical operation in order to measure a shape of the subject; an imaging step of converting measurement light source light images of the plurality of bands, which are reflected from a surface and an inside of the subject by the irradiation in the light source step, into a plurality of electrical measurement imaging signals; a calculation step of measuring a shape of the surface and a shape of the inside in the subject based on the plurality of electrical measurement imaging signals obtained through the conversion in the imaging step; and a composition-processing step of composition-processing the shape of the surface and the shape of the inside which are measured in the calculation step to create one of two-dimensional image data and three-dimensional image data about the subject.

Advantageous Effects of Invention

According to the imaging apparatus and the imaging method of the present invention, the result of visible measurement and the result of the near-infrared measurement in are composition-processed to provide not only the naked-eye display for the site of the surgical operation, but also image information which is obtained by superposing the result of the measurement of the shape of the site below the skin by about several millimeters on the naked-eye display. In this way, the imaging method and apparatus for exactly confirming and grasping the shapes and states of the surface and the inside of the subject as the object of the surgical operation can be obtained.

In addition, by displaying these measurement results in the form of the three-dimensional shape of the subject, the operator can stereoscopically grasp the entire image of the subject in a form in which even the site below the skin by about several millimeters is superposed on the naked-eye image, and hence the operator can response to the more highly-advanced fine surgical operation.

DESCRIPTION OF EMBODIMENTS

An imaging apparatus serving as a medical microscope according to an exemplary embodiment of the present invention is hereinafter described with reference to the drawings.

First Embodiment

Figure 1:
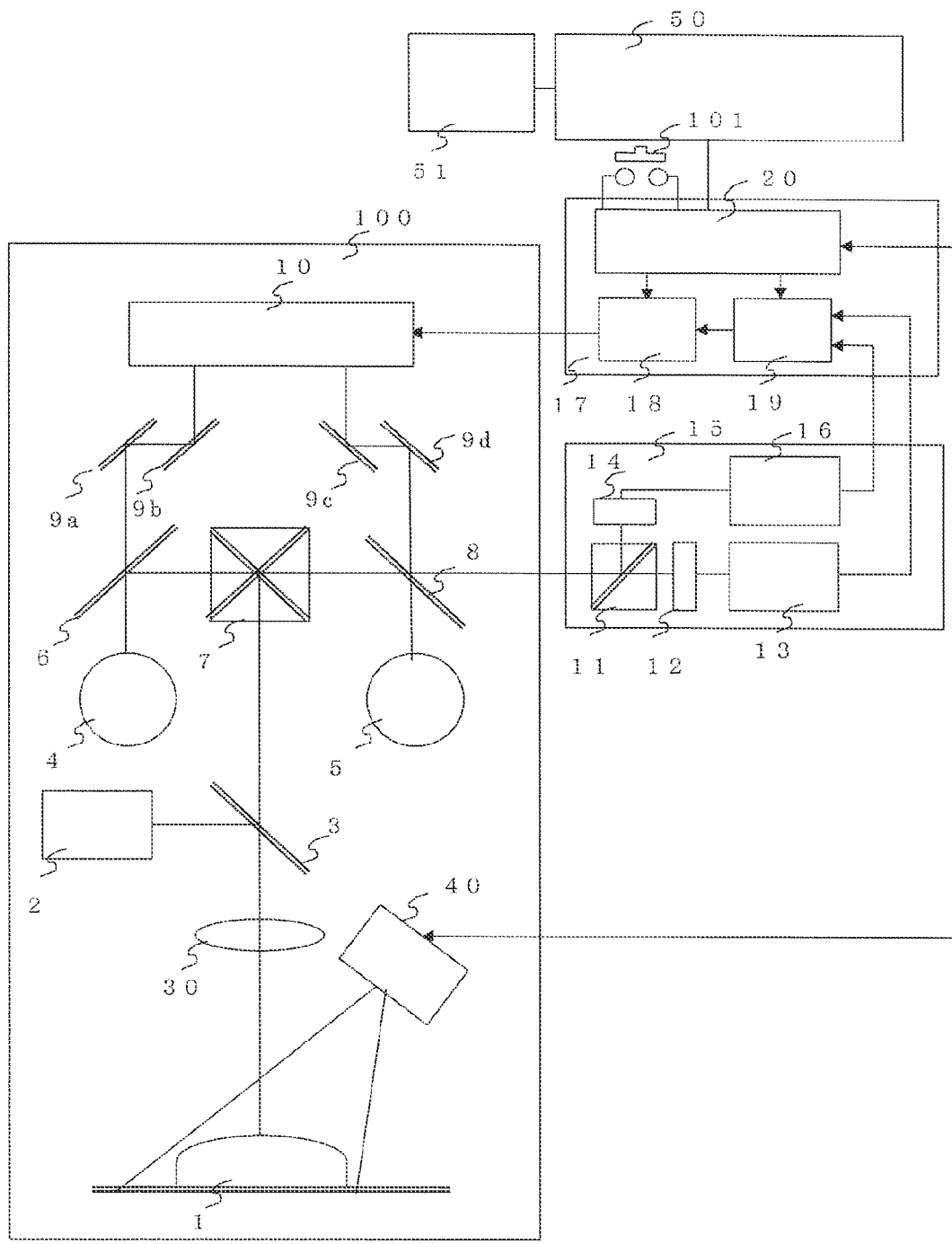
FIG. 1 is a block diagram of an entire imaging apparatus in a first embodiment of the present invention.

FIG. 1 is a block diagram of an entire imaging apparatus in a first embodiment of the present invention. In addition, FIG. 2 is a block diagram illustrating details of an irradiation structure of FIG. 1 in the imaging apparatus in the first embodiment of the present invention.

Figure 2:
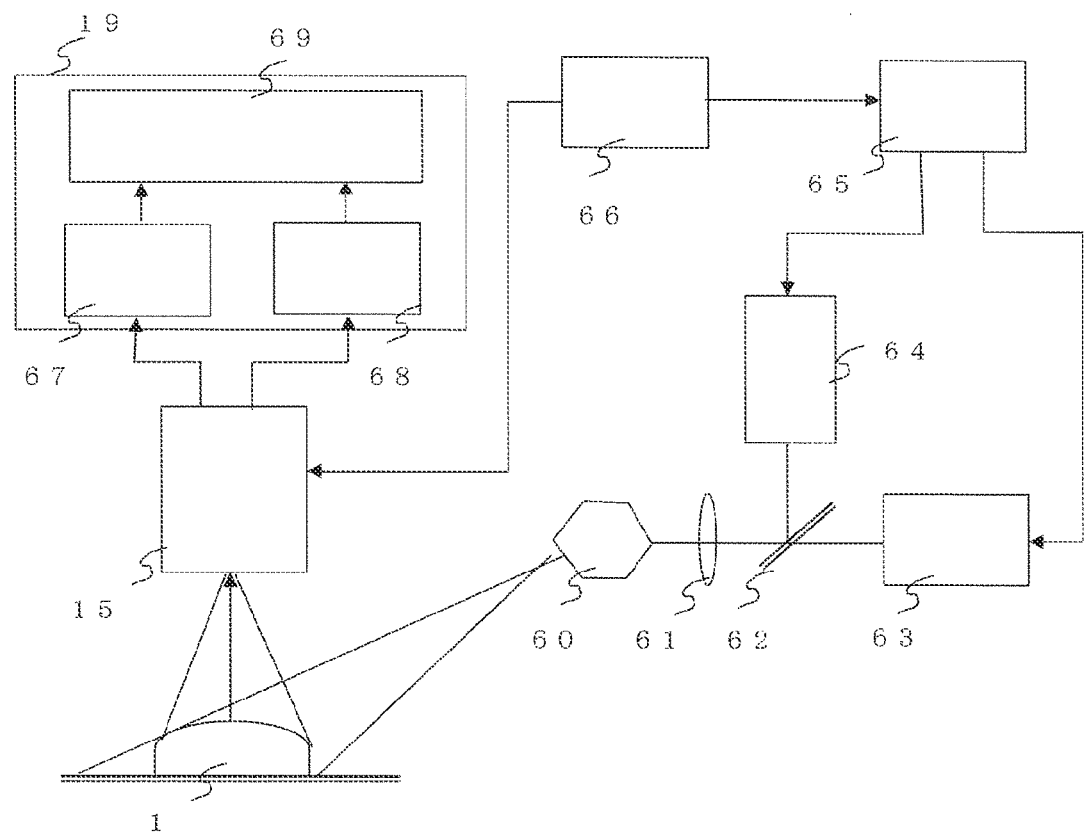
FIG. 2 is a block diagram illustrating details of an irradiation structure of FIG. 1 in the imaging apparatus in the first embodiment of the present invention.

Firstly, configurations of FIG. 1 and FIG. 2 are described with reference to characteristics of FIG. 3 which are described later. In FIG. 1, a light source 40 for three-dimensional measurement which irradiates a subject 1 with light, an ordinary light source 2, an object lens 30, and a dichroic mirror 3 for illumination are installed on a lower side of a main dichroic mirror 7 in a microscope chassis 100.

In addition, in normal macroscopy, a light image of the subject 1 which is obtained by vertical illumination from the ordinary light source 2 is transmitted through a left dichroic mirror 6 for macroscopy and a right dichroic mirror 8 for macroscopy to be imaged on a left eye piece section 4 and a right eye piece section 5. On the other hand, after an optical axis for imaging is reflected by the main dichroic mirror 7, the optical axis for imaging is spectrally diffracted by a beam splitter 11 for imaging.

Here, visible light of the spectrally diffracted light is imaged on a visible imaging sensor 12, and near-infrared light thereof is imaged on a near-infrared imaging sensor 14.

In addition, the visible light processed in a visible signal processing circuit 13, and the near-infrared light processed in a near-infrared signal processing circuit 16 are both sent to a composition processing block 19.

After the composition processing, a resulting signal passes through an output circuit 18 to be output to the outside, and hence an image can be seen on an external monitor. In an example of FIG. 1, after the signal subjected to the composition processing is returned back to an image display device 10 on a microscope side, the image can be seen at the eye piece sections 4, 5 through mirrors 9a, 9b, 9c, and 9d for display. Note that, for the sake of special signal processing or image display in the outside, the imaging apparatus can be connected to a general-purpose personal computer (hereinafter referred to as a PC) 50, and the output from the output circuit 18 can be displayed on a PC monitor 51 connected to the PC 50.

In addition, in FIG. 2, there are installed a laser controller 65 for controlling an irradiation pattern of a visible laser light source 63 and an irradiation pattern of a near-infrared laser light source 64, and a synchronizing circuit 66 for counting an imaging timing synchronized with an imaging unit 15. After laser beams from the two light sources are optically mixed with each other by a dichroic mirror 62 for light source mixing, the resulting light beam is sent to a polygon mirror 60 through a condenser lens 61, and is radiated to the subject 1 in correspondence to the rotation of the polygon mirror 60.

Figure 3:
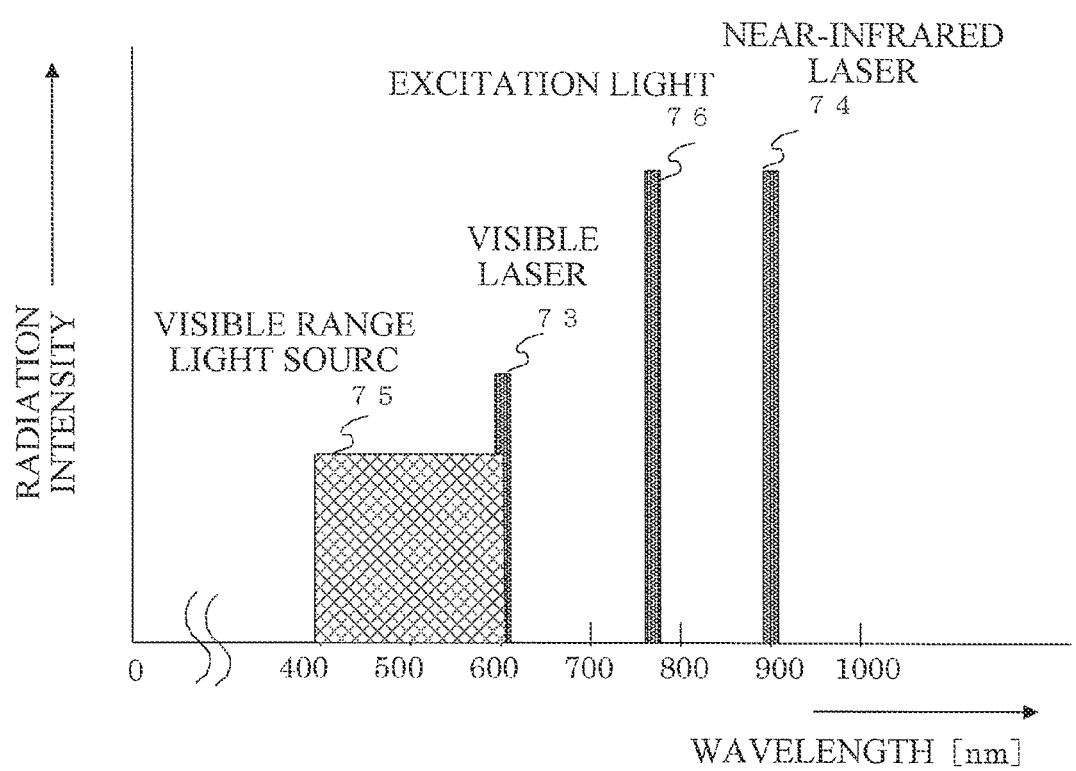
FIG. 3 is a graph showing characteristics of light sources used in the imaging apparatus in the first embodiment of the present invention.

FIG. 3 is a graph showing characteristics of the light sources used in the imaging apparatus in the first embodiment of the present invention. The visible laser light source 63 uses, for example, a laser beam having a wavelength of 600 nm, which is radiated with the characteristics as shown in a visible laser 73 of FIG. 3. In addition, the near-infrared laser light source 64 uses, for example, a laser beam having a wavelength of 900 nm, which is radiated with the characteristics as shown in a near-infrared laser 74 of FIG. 3.

Next, an operation of the imaging apparatus in the first embodiment is described with reference to FIG. 1 and FIG. 2. A high-speed and highly-precise general space coding method is utilized as a three-dimensional measurement method. The space coding method is a technique with which points of the space as the object of the measurement are coded with a binary code, and a distance image is collected at the certain number of times of the projection. A pattern at a predetermined pitch of light and dark is projected from the light source, and a projected pattern is successively changed so that the light and dark pitch is changed so as to be doubled at a certain time interval.

A transmission section for the light and a non-transmission section for the light are denoted as 1 and 0, respectively, and hence the pattern of the projected light is subjected to the binary coding. This pattern image is captured with a camera, and is processed synchronously with the phase of the irradiation, to thereby enable a distance to the subject 1 to be known.

Figure 4:
FIG. 4 is a view illustrating a space coding method by the imaging apparatus in the first embodiment of the present invention.
Figure 4:
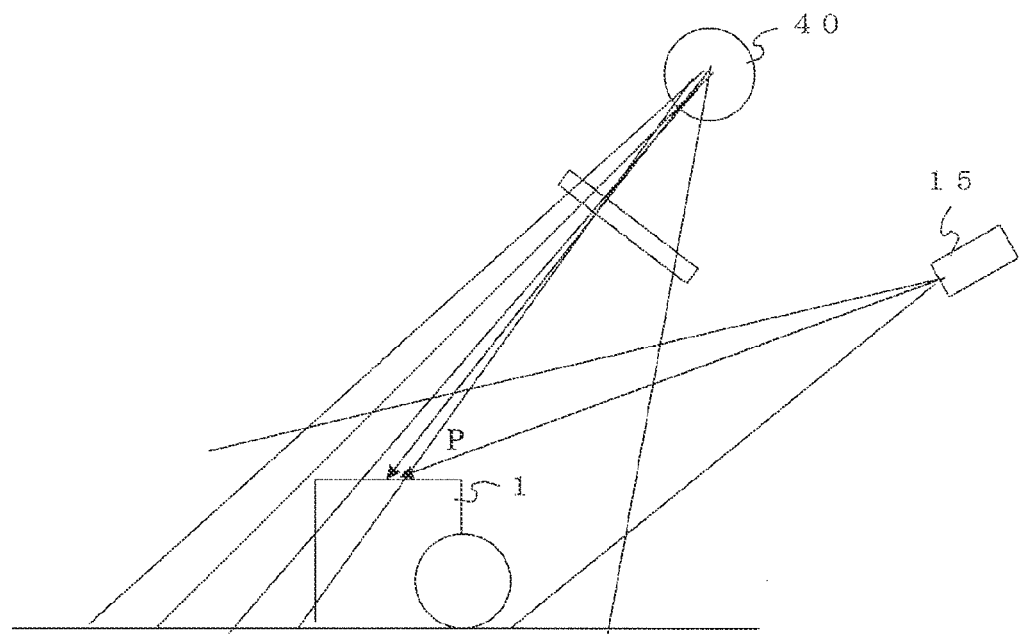

FIG. 4 is a view illustrating the space coding method by the imaging apparatus in the first embodiment of the present invention. For example, a projection pattern at a point P as a fifth region in FIG. 4 is imaged with the imaging unit 15 to know a projection direction, to thereby obtain a projection angle of the light source 40 for three-dimensional measurement. For this reason, the distance can be known.

Next, an actual three-dimensional measurement operation is described. Firstly, for start of the measurement, an operator depresses a start button 101. To carry out the three-dimensional measurement in the visible region on the assumption of the naked eye with the depression of the start button 101 as a trigger, the visible laser light source 63 is driven through the laser controller 65. At this time, the laser controller 65 sends a trigger for start of the imaging to the imaging unit 15 through the synchronizing circuit 66.

The laser controller 65 causes a first projection pattern to be projected on the subject 1 through the visible laser light source 63 and the polygon mirror 60. A positional relationship and the number of rotations of the polygon mirror 60 are determined so that a pattern is projected on the entire subject in a certain range. A first projection pattern image which is obtained from the subject 1 is transmitted through the main dichroic mirror 7 and the beam splitter 11 for imaging to be formed on the visible imaging sensor 12.

In addition, the imaged visible signal is sent to a visible shape calculation circuit 68 in the composition processing block 19 through the visible signal processing circuit 13, and data fetching is started in a control circuit 20. The laser controller 65 and the visible laser light source 63 cause a next projection pattern to be projected on the subject 1, and similarly, the fetching of additional data is carried out in the visible shape calculation circuit 68 and the control circuit 20. After all the projection patterns are similarly projected, the synchronizing circuit 66 sends a trigger for end to the imaging unit 15.

In addition, at a time point at which the fetching of all the projection patterns is completed, the visible shape calculation circuit 68 calculates a distance to the subject in the visible range. Result information is temporarily stored in a memory in the visible shape calculation circuit.

On the other hand, the near-infrared three-dimensional measurement is also similarly carried out. That is to say, the trigger for start of the imaging is sent to the imaging unit 15 through the synchronizing circuit 66, and the laser controller 65 causes the first projection pattern to be projected on the subject 1 through the near-infrared laser light source 64 and the polygon mirror 60. The projection pattern image which is obtained from the subject 1 at this time is transmitted through the main dichroic mirror 7 and the beam splitter 11 for imaging to be formed on the near-infrared imaging sensor 14.

In addition, the imaged near-infrared signal is sent to a near-infrared shape calculation circuit 67 in the composition processing block 19 through the near-infrared signal processing circuit 16, and the data fetching is started in the control circuit 20. The laser controller 65 and the near-infrared laser light source 64 cause the next projection pattern to be projected on the subject 1, and the fetching of the additional data is similarly carried out in the near-infrared shape calculation circuit 67 and the control circuit 20.

All the projection patterns are similarly projected, and then the synchronizing circuit 66 sends a trigger for end to the imaging unit 15. In addition, at a time point at which the fetching of all the projection patterns is completed, the near-infrared shape calculation circuit 67 calculates a distance to the subject in the near-infrared region. Result information is temporarily stored in a memory in the near-infrared shape calculation circuit.

Figure 5:
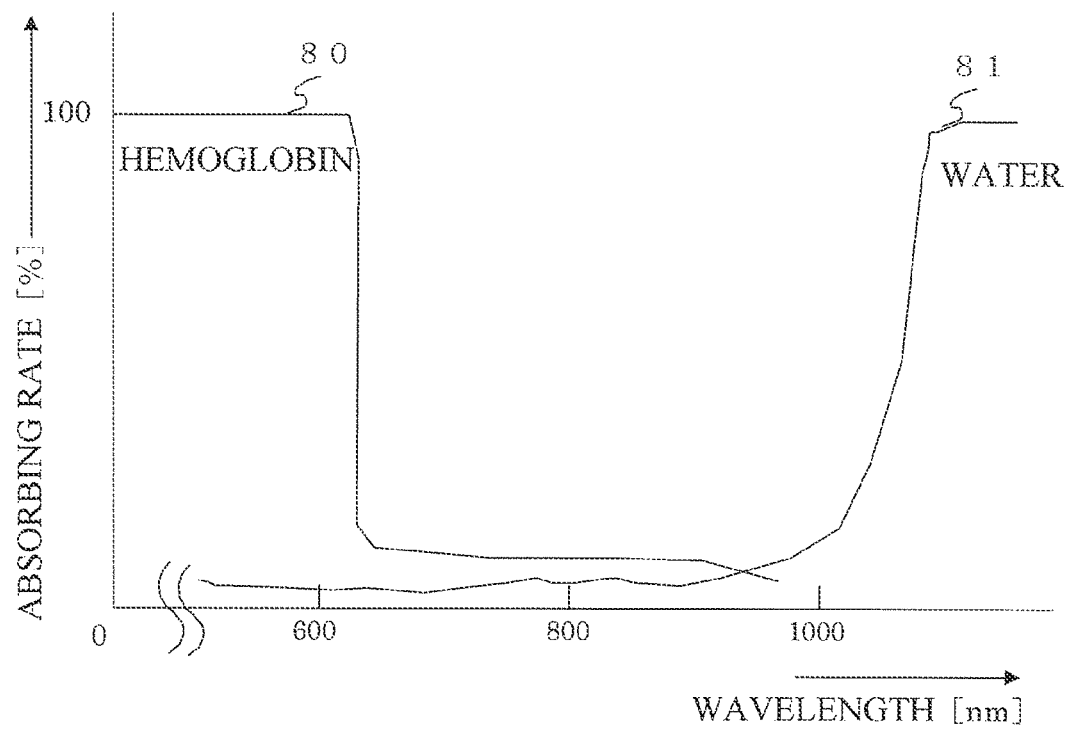
FIG. 5 is a graph showing transmission through a living body at near-infrared wavelengths by the imaging apparatus in the first embodiment of the present invention.

FIG. 5 is a graph showing transmission through a living body at near-infrared wavelengths by the imaging apparatus in the first embodiment of the present invention. It is known that the light in the near-infrared region, as shown in FIG. 5, is transmitted to reach a site below the skin of the living body by about several millimeters in the range of about 700 nm to about 1,200 nm based on absorbing rate characteristics of hemoglobin and moisture in the body. Therefore, when the distance from the subject 1 is measured by utilizing the near-infrared light source, a distance to the site below the skin of the living body by about several millimeters is measured.

Figure 6:
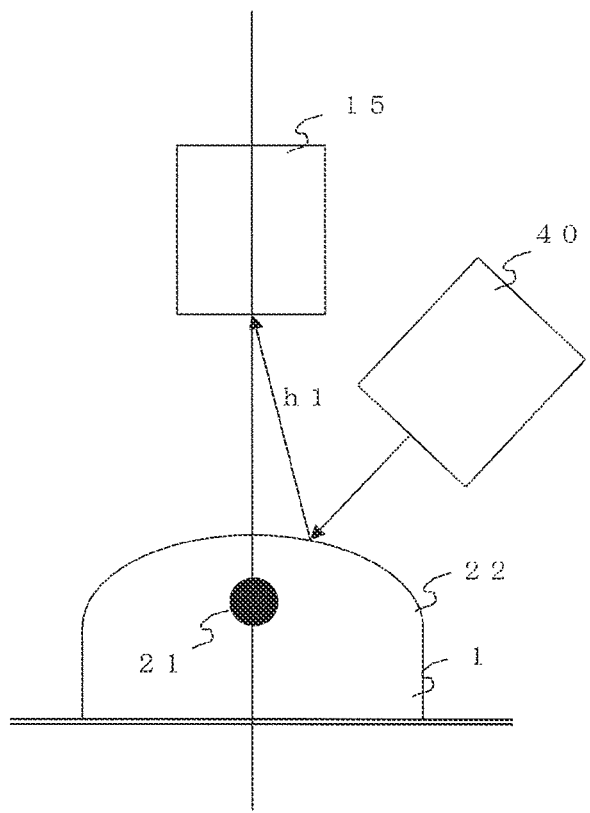
FIG. 6 is a view illustrating visible light measurement by the imaging apparatus in the first embodiment of the present invention.

FIG. 6 is a view illustrating the visible light measurement by the imaging apparatus in the first embodiment of the present invention. As illustrated in FIG. 6, the visible light is reflected by a surface 22 of the subject 1. For this reason, when the distance is measured by using the visible light, a visible distance h1 is obtained.

Figure 7:
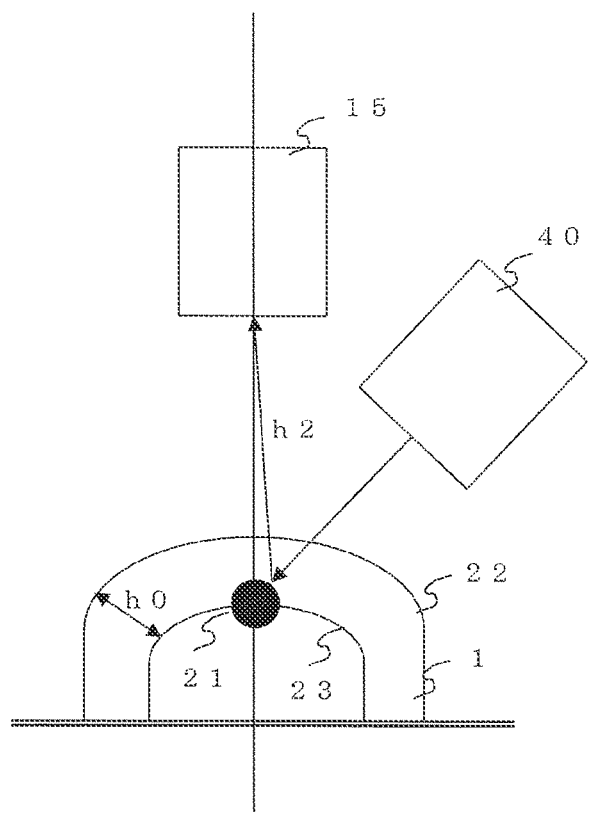
FIG. 7 is a view illustrating near-infrared measurement by the imaging apparatus in the first embodiment of the present invention.

On the other hand, FIG. 7 is a view illustrating the near-infrared measurement by the imaging apparatus in the first embodiment of the present invention. As illustrated in FIG. 7, the near-infrared light is not reflected by the visible surface 22 of the subject 1 of FIG. 7, but is reflected by around a near-infrared surface 23 below the skin by h0 in terms of the living body.

Then, by composing the two pieces of distance measurement data with each other, not only the state which is visible with the naked eye, but also even the site below the skin by several millimeters from the surface can be simultaneously confirmed. That is to say, because the visible measurement result is composed with the near-infrared measurement result, it is possible to provide not only the naked-eye display for the site of the surgical operation, but also the image display obtained by superimposing the result of the distance measurement for the site below the skin by about several millimeters on the naked-eye display. As a result, the blood vessels, the lymph nodes, and the like, which have been hidden and invisible, can be displayed, and hence the risk in the phase of the surgical operation is suppressed.

Note that, although these displays which are two-dimensionally composed with each other by the control circuit 20 in the system may be carried out, because the measurement data itself is the three-dimensional data, the representation of the stereoscopic structure of the subject 1 is preferred so that the subject 1 can be more easily viewed.

Figure 8:
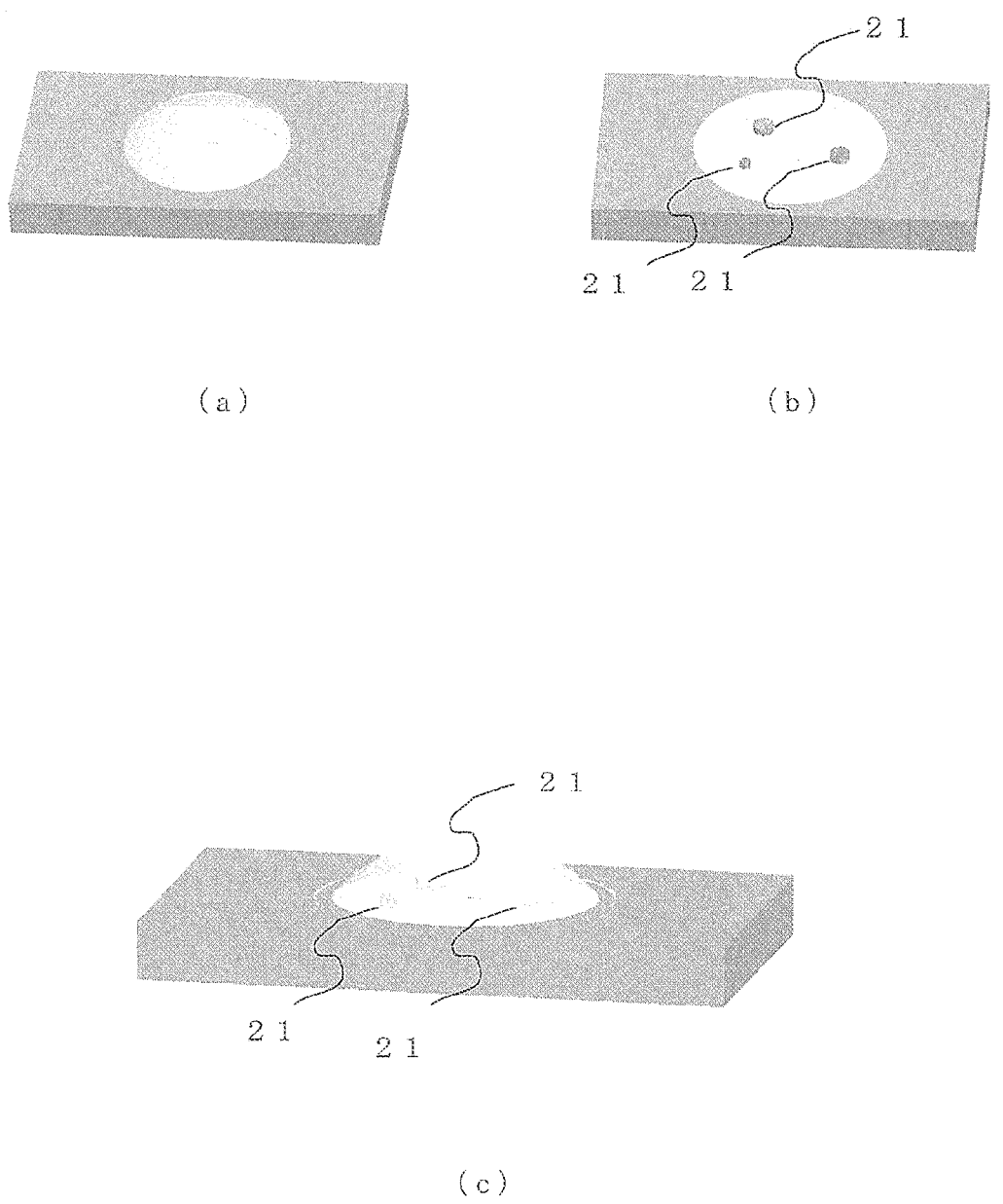
FIGS. 8A to 8C are views each illustrating an example of three-dimensional stereoscopic representation of a subject 1 by composition of results of visible measurement and near-infrared measurement by the imaging apparatus in the first embodiment of the present invention.

FIGS. 8A to 8C are views illustrating an example of three-dimensional stereoscopic representation of the subject 1 by composition of results of visible measurement and near-infrared measurement by the imaging apparatus in the first embodiment of the present invention. FIG. 8A illustrates an example of the three-dimension stereoscopic display from the visible measurement, FIG. 8B illustrates an example of the three-dimension stereoscopic display from the near-infrared measurement, and FIG. 8C illustrates an example of the three-dimensional stereoscopic display by the composition of both the visible measurement result and the near-infrared measurement result. Blood vessels 21 are displayed so as to be readily viewed by FIG. 8C.

As illustrated in previous FIG. 1, the control circuit 20 in the system includes a data interface which is compatible with the PC 50, and can output the measurement data to the outside. In addition, the external PC 50 in which dedicated software is installed can carry out re-calculation and data conversion for the three-dimensional expression, and can display the three-dimensional structure like FIG. 8C on the PC monitor 51.

That is to say, the example (FIG. 8A) of the three-dimensional stereoscopic display from the visible measurement is composed with the example (FIG. 8B) of the three-dimensional stereoscopic display from the near-infrared measurement as the information on the site below the skin by several millimeters to be displayed in the form of FIG. 8C, and hence the subject and the vascular tissue lying inside the subject can be confirmed and grasped from the three-dimensional structure. Thus, this becomes very useful information from a viewpoint of the confirmation of the situations before and after the surgical operation.

Note that, this application software has, for example, a function of being able to store this image in the PC 50, and hence the necessary information can be recorded or taken out when needed. After the operator carries out the process for the measurement at least once before the surgical operation to store the data, the operator can display the image at any time when needed including the phase of the surgical operation to confirm the image.

Note that, although in the above description, the distance measurement using the near-infrared light is carried out after the distance measurement using the visible light, the distance measurement using the near-infrared light may be carried out earlier by changing the order. Alternatively, the configuration of the first embodiment, as illustrated in previous FIG. 1 and FIG. 2, includes the two kinds of light sources for the visible light and the near-infrared light. Therefore, when the calculation result is desired to be hurriedly obtained, the visible measurement and the near-infrared measurement can be carried out at the same time, and as a result, the measurement time can be shortened as compared with the case of the individual measurements.

In addition, it goes without saying that, with respect to the display of the result after the calculation, not only the composition result can be stored and displayed after both the visible measurement and the near-infrared measurement are carried out, but also the results can be individually stored and displayed after the visible measurement and the near-infrared measurement are each carried out.

In addition, the wavelength of 600 nm and the wavelength of 700 nm are used in the visible light measurement and the near-infrared measurement, respectively. For example, alternatively, another wavelength may be selected so as to correspond to the sensitivity characteristics of the imaging element, and if the pattern projection can be carried out, another light source such as the LED may be used instead of the laser.

In addition, although the two kinds of light sources for the visible light and the near-infrared light are used as the light sources for the measurement, the present invention is not limited thereto, and for the more detailed measurement, the measurement may be carried out by using three or more kinds of light sources. Moreover, the light source 40 for three-dimensional measurement and the ordinary light source 2 for ordinary observation can be used in a sharing manner, and hence any one of them can be omitted without any problem.

In addition, for the pattern projection from start to end when the three-dimensional measurement is carried out by using the space patterning method, any of patterns may be used. In addition, for the number of times of the pattern projection, and the number of sheets of fetched images for a time period of the pattern projection, any value may be taken as long as there is no physical or temporal restriction. Although the measurement of the distance to the subject is utilized in the measurement of the shape of the subject, it goes without saying that a method such as a contour method other than the distance measurement may be used as long as the shape measurement can be carried out including the visible measurement or the near-infrared measurement. Moreover, although in the first embodiment, the example of application to the microscope is described, the present invention may also be applied to a hard mirror, an endoscope, a macro-camera, or the like.

In addition, as the technique for expressing the three-dimensional measurement information on the visible measurement and the near-infrared measurement, the present invention is not limited to the three-dimensional stereoscopic structure. Thus, any technique may be used as long as the three-dimensional measurement information on the visible measurement and the near-infrared measurement is displayed by using a two-dimensional expression technique or other expression technique which is easy for an operator to understand.

In addition, although in the first embodiment described above, the two kinds of imaging elements are used in the visible measurement and the near-infrared measurement, it goes without saying that, if an imaging sensor having a wide band and high sensitivity is used, then, one kind of sensor only has to be used. In addition, two or more kinds of imaging sensors may be used in order to ensure the band necessary for the measurement.

Further, although in the foregoing, the three-dimensional composition display of the results of the visible distance measurement and the near-infrared distance measurement is carried out in the external PC 50, the three-dimensional composition display may be carried out in the control circuit 20. At this time, any of the display methods and places for the results may be adopted such as displaying the results not only on the external monitor 51, but also on display means inside the microscope.

Second Embodiment

Figure 9:
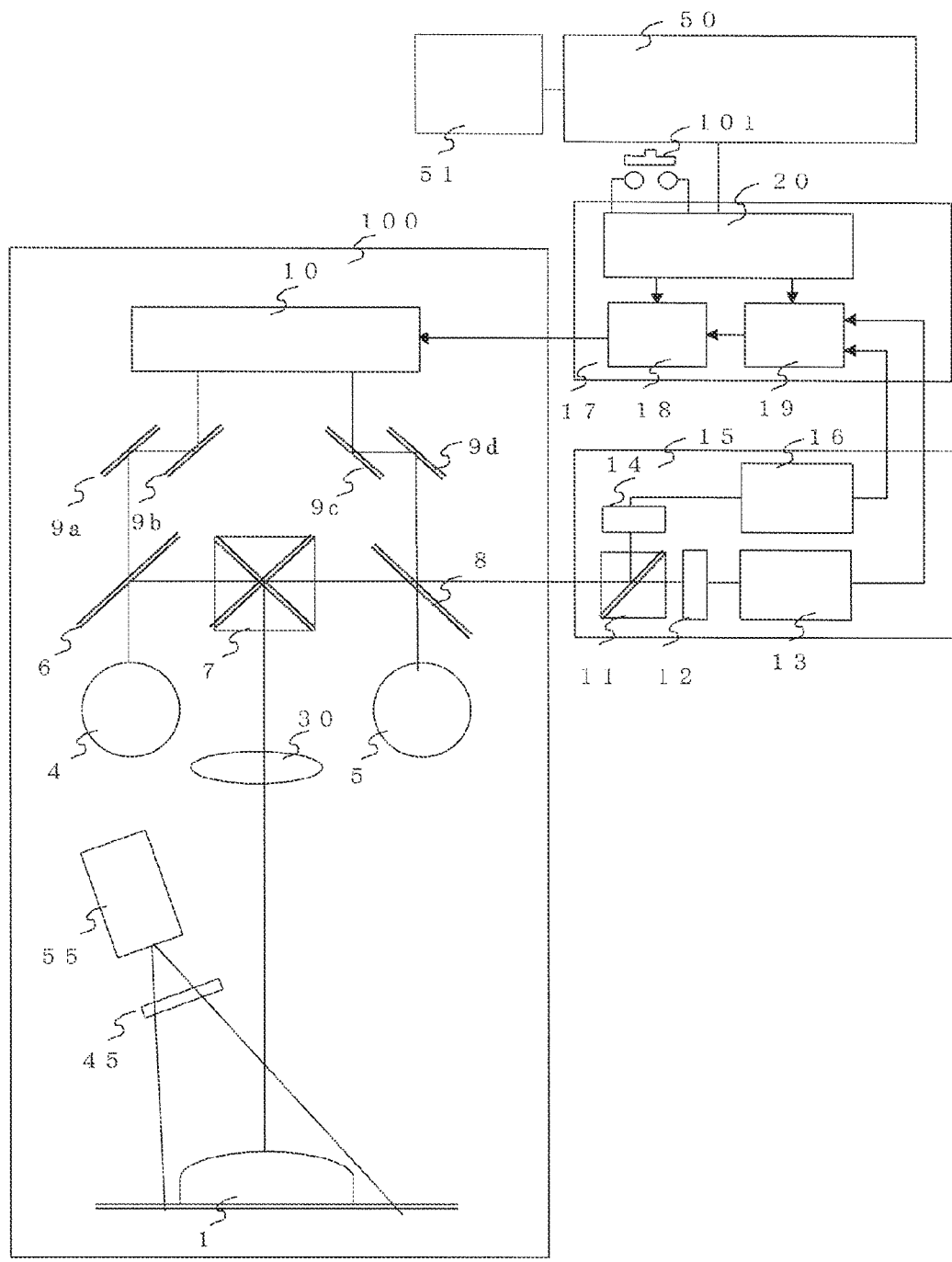
FIG. 9 is a block diagram of an entire imaging apparatus in a second embodiment of the present invention.

FIG. 9 is a block diagram of an entire imaging apparatus in a second embodiment of the present invention. In addition, FIG. 10 is a block diagram illustrating details of an irradiation structure of FIG. 9 in the imaging apparatus in the second embodiment of the present invention.

Figure 10:
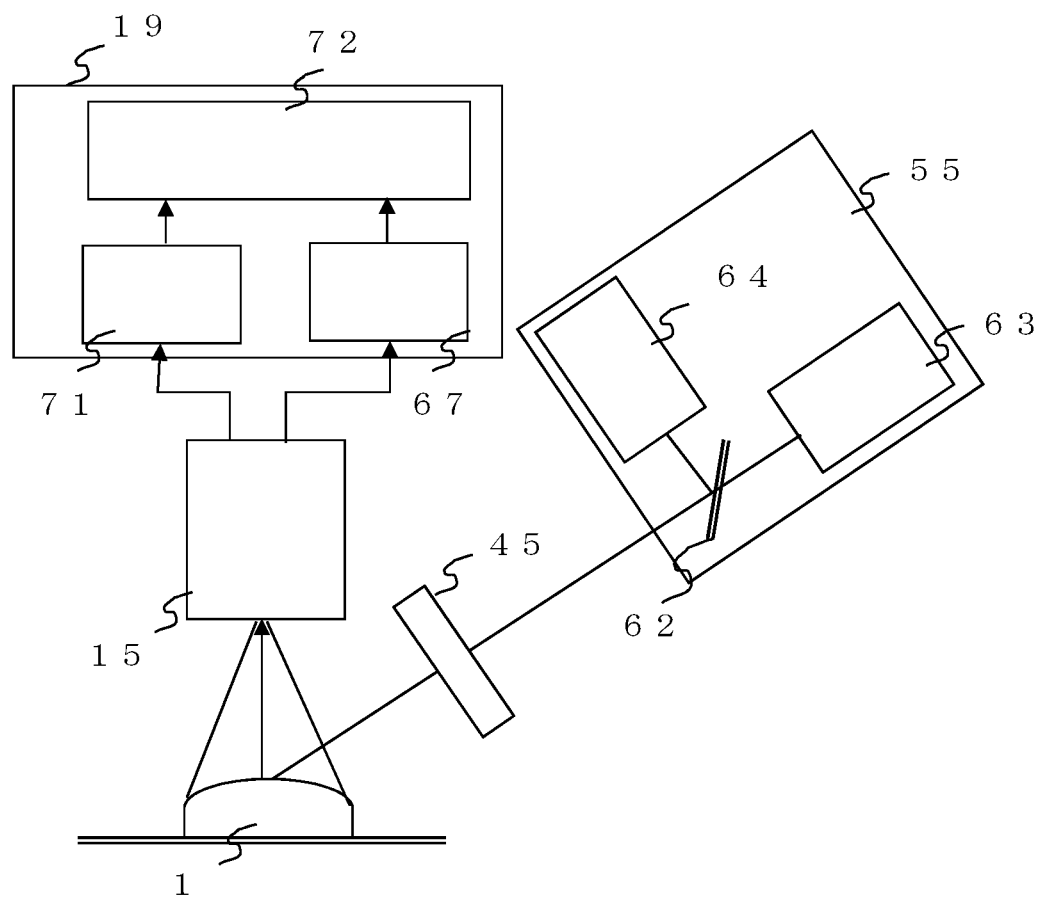
FIG. 10 is a block diagram illustrating details of an irradiation structure of FIG. 9 in the imaging apparatus in the second embodiment of the present invention.

Firstly, configurations of FIG. 9 and FIG. 10 are described with reference to the characteristics of FIG. 3 described above. In FIG. 9, a light source 55 for three-dimensional measurement which irradiates the subject 1 with light, the object lens 30, and the dichroic mirror 3 for the illumination are installed on the lower side of the main dichroic mirror 7 in the microscope chassis 100. Further, the light source 55 for three-dimensional measurement is used also in formal macroscopy.

The light source 55 for three-dimensional measurement in the phase of the ordinary observation mode operates as an vertical illumination having a wavelength band of about 300 nm to about 700 nm in the visible light. The light from this light source is radiated to the subject 1 through a mirror 48 (not shown). A lattice plate 45 which is used in the phase of the three-dimensional measurement can be disposed between the mirror 48 and the subject 1. In the actual structure, the lattice plate 45 is not disposed in the phase of the ordinary observation, but is disposed in a predetermined position of FIG. 9 and FIG. 10 in the phase of the three-dimensional measurement by hand.

The light image of the subject 1 which is obtained by this light source is transmitted through the left dichroic mirror 6 for macroscopy and the right dichroic mirror 8 for macroscopy to be imaged on the left eye piece section 4 and the right eye piece section 5. On the other hand, after an optical axis for imaging is reflected by the main dichroic mirror 7, the optical axis for imaging is spectrally diffracted by the beam splitter 11 for imaging.

Here, visible light of the spectrally diffracted light is imaged on the visible imaging sensor 12, and near-infrared light thereof is imaged on the near-infrared imaging sensor 14. In addition, the visible light processed in the visible signal processing circuit 13, and the near-infrared light processed in the near-infrared signal processing circuit 16 are both sent to the composition processing block 19.

After the composition processing, a resulting signal passes through the output circuit 18 to be output to the outside, and hence an image can be seen on an external monitor. In an example of FIG. 9, after the signal subjected to the composition processing is returned back to the image display device 10 on the microscope side, the image can be seen at the eye piece sections 4, 5 through the mirrors 9*a*, 9*b*, 9*c*, and 9*d* for display. Note that, for the sake of special signal processing or image display in the outside, the imaging apparatus can be connected to the general-purpose PC 50, and the output from the output circuit 18 can be displayed on the PC monitor 51 connected to the PC 50.

In addition, in FIG. 10, after the two laser beams from the visible laser light source 63 and the near-infrared laser light source 64 are mixed with each other in the dichroic mirror 62 for light source mixing, the resulting light beam is radiated to the subject 1 through the lattice plate 45. The visible laser light source 63 uses, for example, a laser beam having a wavelength of 600 nm, which is radiated with the characteristics as shown in the visible laser 73 of previous FIG. 3. In addition, the near-infrared laser light source 64 uses, for example, a laser beam having a wavelength of 900 nm, which is radiated with the characteristics as shown in the near-infrared laser 74 of FIG. 3.

Next, an operation of the imaging apparatus in the second embodiment is described with reference to FIG. 9 and FIG. 10. A moire interference method is used as a three-dimensional measurement method. In the moire interference method, when the lattice plate 45 is disposed in the front of the subject 1, the light is applied from a light source to the lattice plate 45, and the eyes are put in the same position from the lattice 45 as that of the light source, contour fringes as the three-dimensional information showing the shape of the subject 1 can be confirmed on the surface of the subject.

Next, an actual three-dimensional measurement operation is described. Firstly, for start of the measurement, an operator depresses the start button 101. At this time, because the visible laser light source 63 and the near-infrared laser light source 64 need not to be especially controlled, both the visible laser light source 63 and the near-infrared laser light source 64 simultaneously emit laser beams at the wavelength spectra represented by the visible laser 73 and the near-infrared laser 74 as shown in previous FIG. 3.

By the illumination from the visible laser light source 63, the visible wavelength region, in a word, the interference fringes which can be confirmed by the naked eyes can be confirmed on the subject 1. This light image is transmitted through the main dichroic mirror 7 and the beam splitter 11 for imaging to be formed on the visible imaging sensor 12.

In addition, the imaged visible signal is sent to a visible contour calculation circuit 71 in the composition processing block 19 through the visible signal processing circuit 13, and the shape of the subject from the visible measurement is calculated in the visible contour calculation circuit 71. The three-dimensional measurement information in the visible region as the result information is stored in the memory in the visible contour calculation circuit by the control circuit 20.

On the other hand, the near-infrared three-dimensional measurement is also similarly carried out. That is to say, by the illumination from the near-infrared laser light source 63, the near-infrared wavelength region, in a word, the interference fringes in the state in which the laser beam is transmitted to reach the site below the skin by several millimeters can be confirmed on the subject 1. This light image is transmitted through the main dichroic mirror 7 and the beam splitter 11 for imaging to be formed on the near-infrared imaging sensor 14.

Then, the imaged near-infrared signal is sent to the near-infrared shape calculation circuit 67 in the composition processing block 19 through the near-infrared signal processing circuit 16. Then, the shape of the subject from the near-infrared measurement is calculated in the near-infrared shape calculation circuit 67. In addition, the three-dimensional measurement information in the near-infrared region as the result information is stored in the memory in the near-infrared shape calculation circuit by the control circuit 20.

Here, it is known that the light in the near-infrared region, as shown in previous FIG. 5, is transmitted to reach a site below the skin of the living body by about several millimeters in the range of about 700 nm to about 1,200 nm based on the absorbing rate characteristics of hemoglobin and moisture in the body.

Figure 11:
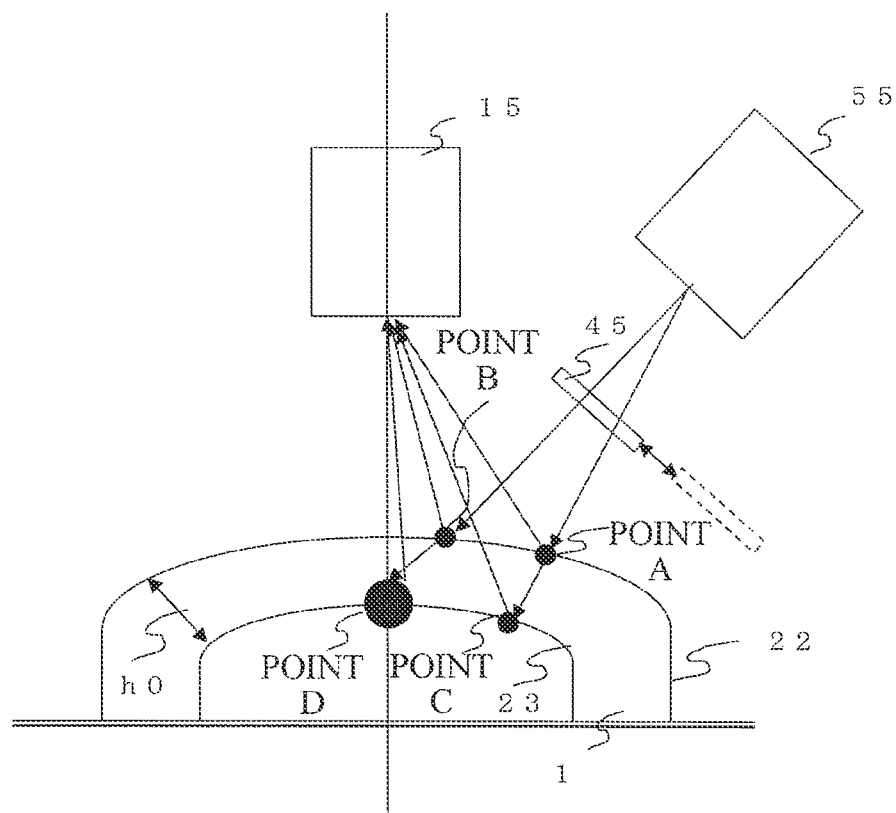
FIG. 11 is a view illustrating visible and near-infrared measurement by the imaging apparatus of the second embodiment of the present invention.

FIG. 11 is a view illustrating visible and near-infrared measurement by the imaging apparatus of the second embodiment of the present invention. As illustrated in FIG. 11, the visible light is reflected by the surface 22 of the subject 1. For this reason, the contour by the light source 55, for example, can be confirmed on a surface of a point A and a point B based on a positional relationship with the imaging unit 15, whereas the contour in the near-infrared region, for example, can be confirmed on a surface of a point C and a point D.

Even when the shape from the subject 1 is measured by utilizing the near-infrared light source by using the moire interference method in such a manner, the shape of the site below the skin by about several millimeters in the living body can be measured. By composing the two pieces of measurement data with each other, not only the state visible with the naked eye, but even a site below the skin by several millimeters from the surface can be simultaneously confirmed. That is to say, because the visible measurement result is composed with the near-infrared measurement result, it is possible to provide not only the naked-eye display for the site of the surgical operation, but also the image display obtained by superimposing the result of the measurement for the site below the skin by about several millimeters on the naked-eye display. As a result, the shapes of the blood vessels, the lymph nodes, and the like, which have been hidden and invisible, can be displayed, and hence the risk in the phase of the surgical operation is suppressed.

Note that, although these displays which are two-dimensionally composed with each other by the control circuit 20 in the system may be carried out, because the measurement data itself is the three-dimensional data, the representation of the stereoscopic structure of the subject 1 is preferred so that the subject 1 can be more easily viewed. More specifically, like FIGS. 8A to 8C described in the previous first embodiment, the three-dimensional stereoscopic display by the composition of the results in both the visible measurement and the near-infrared measurement can be carried out.

As illustrated in previous FIG. 5, the control circuit 20 in the system includes the data interface which is compatible with the PC 50, and can output the measurement data to the outside. In addition, the external PC 50 in which the dedicated software is installed can carry out the re-calculation and the data conversion for the three-dimensional expression, and can display the three-dimensional structure like FIG. 8C on the PC monitor 51.

That is to say, the example (FIG. 8A) of the three-dimensional stereoscopic display from the visible measurement is composed with the example (FIG. 8B) of the three-dimensional stereoscopic display from the near-infrared measurement as the information on the site below the skin by several millimeters to be displayed in the form of FIG. 8C, and hence the subject and the vascular tissue lying inside the subject can be confirmed and grasped from the three-dimensional structure. Thus, this becomes very useful information from a viewpoint of the confirmation of the situations before and after the surgical operation.

Note that, this application software has, for example, a function of being able to store this image in the PC 50 the like, and hence the necessary information can be recorded or taken out when needed. After the operator carries out the process for the measurement at least once before the surgical operation to store the data, the operator can display the image at any time when needed including the phase of the surgical operation to confirm the image.

Note that, although in the above description, the measurement using the near-infrared light is carried out after the measurement using the visible light, the measurement using the near-infrared light may be carried out earlier by changing the order. Alternatively, the configuration of the second embodiment, as illustrated in previous FIG. 9 and FIG. 10, includes the two kinds of light sources for the visible light and the near-infrared light. Therefore, when the calculation result is desired to be hurriedly obtained, the visible measurement and the near-infrared measurement can be carried out at the same time, and as a result, the measurement time can be shortened as compared with the case of the individual measurements.

In addition, it goes without saying that, with respect to the display of the result after the calculation, not only the composition result can be stored and displayed after both the visible measurement and the near-infrared measurement are carried out, but also the results can be individually stored and displayed after the visible measurement and the near-infrared measurement are each carried out.

In addition, the wavelength of 600 nm and the wavelength of 700 nm are used in the visible light measurement and the near-infrared measurement, respectively. For example, alternatively, another wavelength may be selected so as to correspond to the sensitivity characteristics of the imaging element, and if the interference fringes can be confirmed, another light source such as the LED may be used instead of the laser.

In addition, although the two kinds of light sources for the visible light and the near-infrared light are used as the light sources for the measurement, the present invention is not limited thereto, and for the more detailed measurement, the measurement may be carried out by using three or more kinds of light sources.

Moreover, although the light source 40 for three-dimensional measurement and the ordinary light source 2 for ordinary observation are used in the sharing manner, like the characteristics of a visible range light source 75 as shown in FIG. 3, the ordinary light source may also be individually provided.

In addition, although the three-dimensional measurement is carried out by using the moire interference method, any other suitable technique may also be adopted as long as the three-dimensional information can be obtained in the image analysis. Moreover, although in the second embodiment, the example of application to the microscope is described, the present invention may also be applied to the hard mirror, the endoscope, the macro-camera, or the like.

In addition, as the technique for expressing the three-dimensional measurement information on the visible measurement and the near-infrared measurement, the present invention is not limited to the three-dimensional stereoscopic structure. Thus, any technique may be used as long as the three-dimensional measurement information on the visible measurement and the near-infrared measurement is displayed by using the two-dimensional expression technique or other expression technique which is easy for the operator to understand.

In addition, although in the second embodiment described above, the two kinds of imaging elements are used in the visible measurement and the near-infrared measurement, it goes without saying that, if an imaging sensor having a wide band and high sensitivity is used, then, one kind of sensor only has to be used. In addition, two or more kinds of imaging sensors may be used in order to ensure the band necessary for the measurement.

Further, although in the foregoing, the three-dimensional composition display of the results of the visible shape measurement and the near-infrared shape measurement is carried out in the external PC 50, the three-dimensional composition display may be carried out in the control circuit 20. At this time, any of the display methods and places for the results may be adopted such as displaying the results not only on the external monitor 51, but also on the display means inside the microscope.

Third Embodiment

Figure 12:
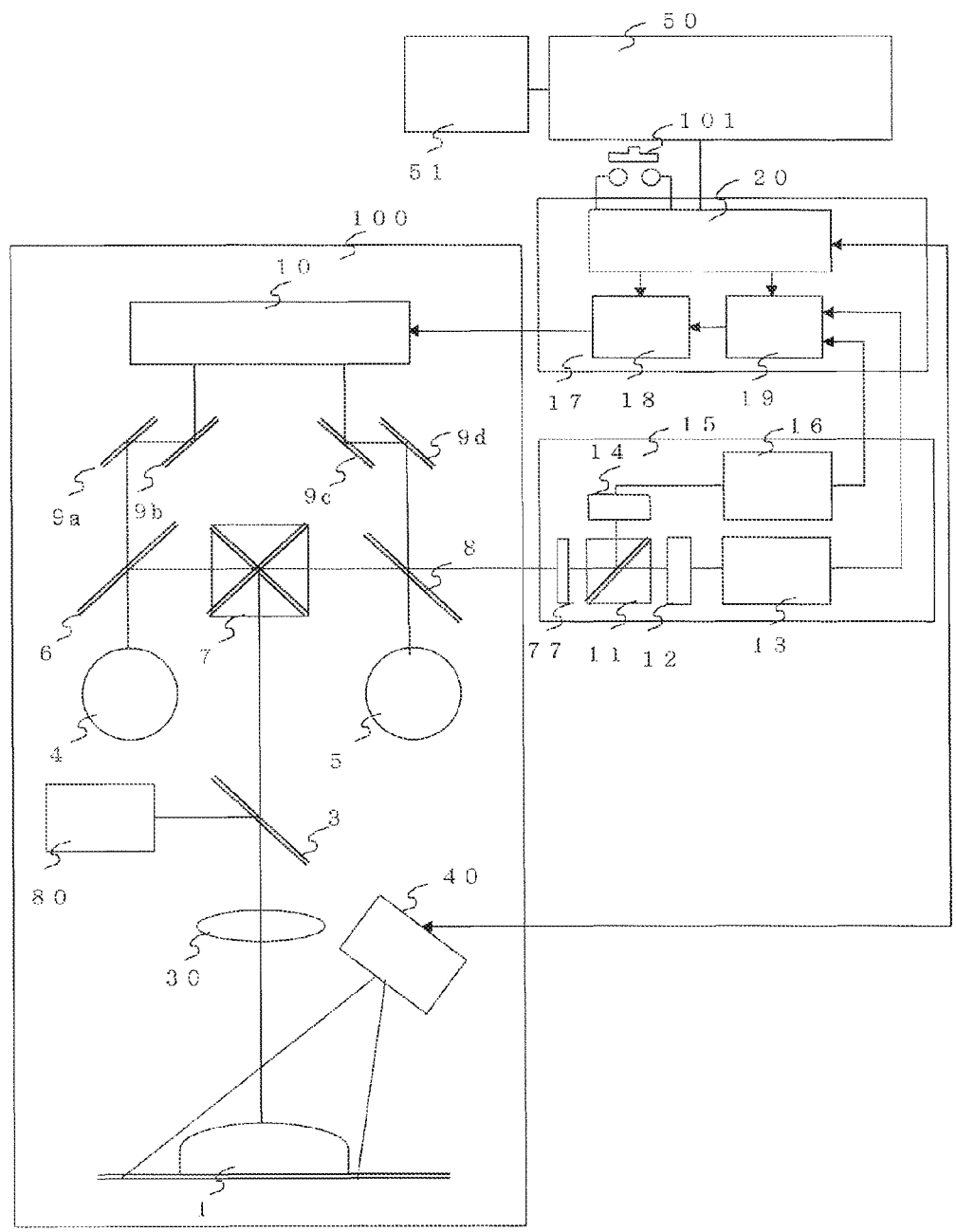
FIG. 12 is a block diagram of an entire imaging apparatus in a third embodiment of the present invention.

FIG. 12 is a block diagram of an entire imaging apparatus in a third embodiment of the present invention. Firstly, a configuration of FIG. 12 is described with reference to the characteristics of FIG. 3 described above. In FIG. 12, the light source 40 for three-dimensional measurement which irradiates the subject 1 with light, an ordinary light source 80 containing excitation light, the object lens 30, and the dichroic mirror 3 for illumination are installed on the lower side of the main dichroic mirror 7 in the microscope chassis 100.

In addition, in normal macroscopy, a light image of the subject 1 which is obtained by vertical illumination from the ordinary light source 80 containing excitation light is transmitted through the left dichroic mirror 6 for macroscopy and the right dichroic mirror 8 for macroscopy to be imaged on the left eye piece section 4 and the right eye piece section 5. On the other hand, after an optical axis for imaging is reflected by the main dichroic mirror 7, the optical axis for imaging is spectrally diffracted by the beam splitter 11 for imaging.

Here, visible light of the spectrally diffracted light is imaged on the visible imaging sensor 12, and near-infrared light thereof is imaged on the near-infrared imaging sensor 14. In addition, the visible light processed in the visible signal processing circuit 13, and the near-infrared light processed in the near-infrared signal processing circuit 16 are both sent to the composition processing block 19.

After the composition processing, a resulting signal passes through the output circuit 18 to be output to the outside, and hence an image can be seen on an external monitor. In an example of FIG. 12, after the signal subjected to the composition processing is returned back to the image display device 10 on the microscope side, the image can be seen at the eye piece sections 4, 5 through the mirrors 9a, 9b, 9c, and 9d for display. Note that, for the sake of special signal processing or image display in the outside, the imaging apparatus can be connected to the general-purpose PC 50, and the output from the output circuit 18 can be displayed on the PC monitor 51 connected to the PC 50.

In addition, in pervious FIG. 2, the laser controller 65 for controlling the irradiation pattern of the visible laser light source 63 and the irradiation pattern of the near-infrared laser light source 64, and the synchronizing circuit 66 for counting an imaging timing synchronized with the imaging unit 15 are installed. After laser beams from the two light sources are optically mixed with each other by the dichroic mirror 62 for light source mixing, the resulting light beam is sent to the polygon mirror 60 through the condenser lens 61, and is radiated to the subject 1 in correspondence to the rotation of the polygon mirror 60.

Further, the visible laser light source 63 uses, for example, a laser beam having a wavelength of 600 nm, which is radiated with the characteristics as shown in the visible laser 73 of previous FIG. 3. In addition, the near-infrared laser light source 64 uses, for example, a laser beam having a wavelength of 900 nm, which is radiated with the characteristics as shown in the near-infrared laser 74 of FIG. 3.

In addition, an illumination light source for emitting excitation light 76 having a wavelength of 770 nm of FIG. 3 is installed in the ordinary light source 80 containing the excitation light. At this time, indocyanine green as a fluorescent material for angiography is administered to the subject 1. The subject 1 absorbs the excitation light 76, and emits fluorescence at about 840 nm. Then, an excitation light cutting filter 77 is mounted to the optical system of the imaging unit 15 of FIG. 12, and hence, of the near-infrared light images, only the fluorescence light images can be imaged.

Next, an operation of the imaging apparatus in the third embodiment is described with reference to FIG. 12. A high-speed and highly-precise general space coding method is utilized as a three-dimensional measurement method similarly to the first embodiment described above. The space coding method is a technique with which points of the space as the object of the measurement are coded with a binary code, and a distance image is collected at the certain number of times of the projection. A pattern at a predetermined pitch of light and dark is projected from the light source, and a projected pattern is successively changed so that the light and dark pitch is changed so as to be doubled at a certain time interval.

A transmission section for the light and a non-transmission section for the light are denoted as 1 and 0, respectively, and hence the pattern of the projected light is subjected to the binary coding. This pattern image is captured with a camera, and is processed synchronously with the phase of the irradiation, to thereby enable a distance to the subject 1 to be known. For example, the projection pattern at the point P as the fifth region in previous FIG. 4 is imaged with the imaging unit 15 to know a projection direction, to thereby obtain the projection angle of the light source 40 for the three-dimensional measurement. For this reason, the distance can be known.

Next, an actual three-dimensional measurement operation is described. Firstly, for start of the measurement, an operator depresses the start button 101. To carry out the three-dimensional measurement in the visible region on the assumption of the naked eye with the depression of the start button 101 as a trigger, the visible laser light source 63 is driven through the laser controller 65. At this time, the laser controller 65 sends a trigger for start of the imaging to the imaging unit 15 through the synchronizing circuit 66.

The laser controller 65 causes a first projection pattern to be projected on the subject 1 through the visible laser light source 63 and the polygon mirror 60. A positional relationship and the number of rotations of the polygon mirror 60 are determined so that a pattern is projected on the entire subject in a certain range. A first projection pattern image which is obtained from the subject 1 is transmitted through the main dichroic mirror 7 and the beam splitter 11 for imaging to be formed on the visible imaging sensor 12.

In addition, the imaged visible signal is sent to the visible shape calculation circuit 68 in the composition processing block 19 through the visible signal processing circuit 13, and data fetching is started in the control circuit 20. The laser controller 65 and the visible laser light source 63 cause a next projection pattern to be projected on the subject 1, and similarly, the fetching of additional data is carried out in the visible shape calculation circuit 68 and the control circuit 20. After all the projection patterns are similarly projected, the synchronizing circuit 66 sends a trigger for end to the imaging unit 15.

In addition, at a time point at which the fetching of all the projection patterns is completed, the visible shape calculation circuit 68 calculates a distance to the subject in the visible range. Result information is temporarily stored in the memory in the visible shape calculation circuit.

On the other hand, the near-infrared three-dimensional measurement is also similarly carried out. That is to say, the trigger for start of the imaging is sent to the imaging unit 15 through the synchronizing circuit 66, and the laser controller 65 causes the first projection pattern to be projected on the subject 1 through the near-infrared laser light source 64 and the polygon mirror 60. The projection pattern image which is obtained from the subject 1 at this time is transmitted through the main dichroic mirror 7 and the beam splitter 11 for imaging to be formed on the near-infrared imaging sensor 14.

In addition, the imaged near-infrared signal is sent to the near-infrared shape calculation circuit 67 in the composition processing block 19 through the near-infrared signal processing circuit 16, and the data fetching is started in the control circuit 20. The laser controller 65 and the near-infrared laser light source 64 cause the next projection pattern to be projected on the subject 1, and the fetching of the additional data is similarly carried out in the near-infrared shape calculation circuit 67 and the control circuit 20.

All the projection patterns are similarly projected, and then the synchronizing circuit 66 sends a trigger for end to the imaging unit 15. In addition, at a time point at which the fetching of all the projection patterns is completed, the near-infrared shape calculation circuit 67 calculates a distance to the subject in the near-infrared region. Result information is temporarily stored in the memory in the near-infrared shape calculation circuit.

Further, a fluorescence (blood vessel) portion achieved by the administration of indocyanine green is collected after the three-dimensional measurement in the pattern projection. The excitation light 76 emitted from the ordinary light source 80 containing excitation light is absorbed by indocyanine green administered to the subject 1, and hence a fluorescence light image is generated at about 840 nm. This fluorescence light image is converted into an electrical signal by using the near-infrared imaging sensor 14 through the excitation light cutting filter 77.

As described in the previous first embodiment as well, it is known that the light in the near-infrared region, as shown in previous FIG. 5, is transmitted to reach the site below the skin of the living body by about several millimeters in the range of about 700 nm to about 1,200 nm based on absorbing rate characteristics of hemoglobin and moisture in the body. Therefore, when the distance from the subject 1 is measured by utilizing the near-infrared light source, a distance to the site below the skin of the living body by about several millimeters is measured.

As illustrated in previous FIG. 6, the visible light is reflected by the surface 22 of the subject 1. For this reason, when the distance is measured by using the visible light, the visible distance h1 is obtained. On the other hand, as illustrated in previous FIG. 7, the near-infrared light is not reflected by the visible surface 22 of the subject of FIG. 1, but is reflected by around the near-infrared surface 23 below the skin by h0 in terms of the living body. Then, by composing the two pieces of distance measurement data with each other, not only the state visible with the naked eye, but even the site below the skin by several millimeters from the surface can be simultaneously confirmed.

That is to say, because the visible measurement result is composed with the near-infrared measurement result, it is possible to provide not only the naked-eye display for the site of the surgical operation, but also the image display obtained by superimposing the result of the distance measurement for the site below the skin by about several millimeters on the naked-eye display. As a result, the blood vessels, the lymph nodes, and the like, which have been hidden and invisible, can be displayed, and hence the risk in the phase of the surgical operation is suppressed.

Further, in the third embodiment, to more specify the blood vessels, the fluorescence (blood vessel) portion achieved by the administration of indocyanine green can be superimposed on the measurement results described above to be displayed.

Note that, although these displays which are composed in the two-dimensional manner be the control circuit 20 in the system may be carried out, because the measurement data itself is the three-dimensional data, it is preferred to express the measurement data in the form of the stereoscopic structure of the subject 1 so as to be easily viewed. More specifically, like FIGS. 8A to 8C described in the previous first embodiment, the three-dimensional stereoscopic display by the composition of both the result of the visible measurement and the result of the near-infrared measurement can be carried out.

As illustrated in previous FIG. 12, the control circuit 20 in the system includes the data interface which is compatible with the PC 50, and can output the measurement data to the outside. In addition, the external PC 50 in which dedicated software is installed can carry out re-calculation and data conversion for the three-dimensional expression, and can display the three-dimensional structure like FIG. 8C on the PC monitor 51.

That is to say, the example (FIG. 8A) of the three-dimensional stereoscopic display from the visible measurement is composed with the example (FIG. 8B) of the three-dimensional stereoscopic display from the near-infrared measurement as the information on the site below the skin by several millimeters to be displayed in the form of FIG. 8C, and hence the subject and the vascular tissue lying inside the subject can be confirmed and grasped from the three-dimensional structure. Thus, this becomes very useful information from a viewpoint of the confirmation of the situations before and after the surgical operation.

At this time, in the third embodiment, the composition display, including the blood vessel specification result, by the administration of an indocyanine green fluorescent material is carried out, to thereby more specify the blood vessels. Hence, the structure of the subject is easier for the operator to understand.

Note that, this application software has, for example, a function of being able to store this image in the PC 50, and hence the necessary information can be recorded or taken out when needed. After the operator carries out the process for the measurement at least once before the surgical operation to store the data, the operator can display the image at any time when needed including the phase of the surgical operation to confirm the image.

Note that, although in the above description, the distance measurement using the near-infrared light is carried out after the distance measurement using the visible light, the distance measurement using the near-infrared light may be carried out earlier by changing the order. Alternatively, the configuration of the third embodiment, as illustrated in previous FIG. 12, includes the two kinds of light sources for the visible light and the near-infrared light. Therefore, when the calculation result is desired to be hurriedly obtained, the visible measurement and the near-infrared measurement can be carried out at the same time, and as a result, the measurement time can be shortened as compared with the case of the individual measurements.

In addition, it goes without saying that, with respect to the display of the result after the calculation, not only the composition result can be stored and displayed after both the visible measurement and the near-infrared measurement are carried out, but also the results can be individually stored and displayed after the visible measurement and the near-infrared measurement are each carried out.

In addition, the wavelength of 600 nm and the wavelength of 870 nm are used in the visible light measurement and the near-infrared measurement, respectively. For example, alternatively, another wavelength may be selected so as to correspond to the sensitivity characteristics of the imaging element, and if the pattern projection can be carried out, another light source such as the LED may be used instead of the laser.

In addition, although the two kinds of light sources for the visible light and the near-infrared light are used as the light sources for the measurement, the present invention is not limited thereto, and for the more detailed measurement, the measurement may be carried out by using three or more kinds of light sources. The excitation light source is required to give consideration to the ordinary light source side, but may or may not give consideration to the light source for measurement. Moreover, the light source 40 for three-dimensional measurement and the ordinary light source 80 containing excitation light for the ordinary observation can be used in a sharing manner, and hence any one of them can be omitted without any problem.

In addition, for the pattern projection from start to end when the three-dimensional measurement is carried out by using the space patterning method, any of patterns may be used. In addition, for the number of times of the pattern projection, and the number of sheets of fetched images for a time period of the pattern projection, any value may be taken as long as there is no physical or temporal restriction. Although the measurement of the distance to the subject is utilized in the measurement of the shape of the subject, it goes without saying that a method such as a contour method other than the distance measurement may be used as long as the shape measurement can be carried out including the visible measurement or the near-infrared measurement. Moreover, although in the third embodiment, the example of application to the microscope is described, the present invention may also be applied to the hard mirror, the endoscope, the macro-camera, or the like.

In addition, as the technique for expressing the three-dimensional measurement information on the visible measurement and the near-infrared measurement, the present invention is not limited to the three-dimensional stereoscopic structure. Thus, any technique may be used as long as the three-dimensional measurement information on the visible measurement and the near-infrared measurement is displayed by using a two-dimensional expression technique or other expression technique which is easy for an operator to understand.

In addition, although in the first embodiment described above, the two kinds of imaging elements are used in the visible measurement and the near-infrared measurement, it goes without saying that if an imaging sensor having a wide band and high sensitivity is used, then, one kind of sensor only has to be used. In addition, two or more kinds of imaging sensors may be used in order to ensure the band necessary for the measurement.

Further, although in the foregoing, the three-dimensional composition display of the results of the visible distance measurement and the near-infrared distance measurement is carried out in the external PC 50, the three-dimensional composition display may be carried out in the control circuit 20. At this time, any of the display methods and places for the results may be adopted such as displaying not only on the external monitor 51, but also on display means inside the microscope.

The invention claimed is:

1. An imaging apparatus, comprising:
   a light source device comprising a light source having a wavelength of a plurality of bands including visible light band and near-infrared band, the light source device being used to measure a shape of a subject as an object of a surgical operation;
   an imaging circuit configured to convert measurement light source light images of the plurality of bands from the light source device into a plurality of electrical measurement imaging signals, the measurement light source light images being reflected from a surface and an inside of the subject;
   a laser controller for controlling an irradiation pattern of the visible light band and an irradiation pattern of the near-infrared band;
   a synchronizing circuit for counting an imaging timing synchronized with the imaging circuit;
   a calculation circuit configured to measure a shape of the surface and a shape of the inside in the subject based on the plurality of electrical measurement imaging signals obtained through the conversion in the imaging circuit; and
   a composition processing circuit configured to composition-process the shape of the surface and the shape of the inside measured by the calculation circuit to create one of two-dimensional image data and three-dimensional image data about the subject.

2. An imaging apparatus according to claim 1, wherein the light source device and the calculation circuit use a distance measuring method by a space coding method.

3. An imaging apparatus according to claim 1, wherein the light source device and the calculation circuit use a moire interference method.

4. An imaging apparatus, comprising:
   a light source device comprising a light source having a wavelength of a plurality of bands including visible light band and near-infrared band, the light source device being used to measure a shape of a subject as an object of a surgical operation;
   an imaging circuit configured to convert measurement light source light images of the plurality of bands from the light source device into a plurality of electrical measurement imaging signals, the measurement light source light images being reflected from a surface and an inside of the subject;
   a calculation circuit configured to measure a shape of the surface and a shape of the inside in the subject based on the plurality of electrical measurement imaging signals obtained through the conversion in the imaging circuit; and
   a composition processing circuit configured to composition-process the shape of the surface and the shape of the inside measured by the calculation circuit to create one of two-dimensional image data and three-dimensional image data about the subject
   wherein the imaging circuit comprises:
   a first imaging circuit configured to convert a light image having a first wavelength band of the measurement light source light images from the light source device into an electrical measurement imaging signal, the light image having the first wavelength band being reflected from the surface of the subject; and
   a second imaging circuit configured to convert a light image having a second wavelength band of the measurement light source light images from the light source device into an electrical measurement imaging signal, the light image having the second wavelength band being reflected from the inside of the subject,
   wherein the calculation circuit comprises:
   a first calculation circuit configured to measure a first shape to the surface in the subject based on the electrical measurement imaging signal obtained through the conversion in the first imaging circuit; and
   a second calculation circuit configured to measure a second shape to the inside in the subject based on the electrical measurement imaging signal obtained through the conversion in the second imaging circuit, and
   wherein the composition processing circuit composition-processes the first shape measured in the first calculation circuit and the second shape measured in the second calculation circuit to create one of the two-dimensional image data and the three-dimensional image data.

5. An imaging apparatus according to claim 4, wherein when a fluorescent material for angiography is administered to the subject, the second imaging circuit converts a fluorescence light image acquired through means for cutting excitation light into an electrical measurement imaging signal.

6. An imaging apparatus according to claim 5, wherein the light source device and the calculation circuit use a distance measuring method by a space coding method.

7. An imaging apparatus according to claim 5, wherein the light source device and the calculation circuit use a moire interference method.

8. An imaging apparatus according to claim 4, wherein the light source device and the calculation circuit use a distance measuring method by a space coding method.

9. An imaging apparatus according to claim 4, wherein the light source device and the calculation circuit use a moire interference method.

10. An imaging method, comprising:
a light source step of carrying out irradiation from a light source having a wavelength of a plurality of bands, including visible light band and near-infrared band, to a subject as an object of a surgical operation in order to measure a shape of the subject;

an imaging step of converting measurement light source light images of the plurality of bands, which are reflected from a surface and an inside of the subject by the irradiation in the light source step, into a plurality of electrical measurement imaging signals;

a laser step of controlling an irradiation pattern of the visible light band and an irradiation pattern of the near-infrared band;

a synchronizing step of counting an imaging timing synchronized with the imaging circuit;

a calculation step of measuring a shape of the surface and a shape of the inside in the subject based on the plurality of electrical measurement imaging signals obtained through the conversion in the imaging step; and a composition-processing step of composition-processing the shape of the surface and the shape of the inside which are measured in the calculation step to create one of two-dimensional image data and three-dimensional image data about the subject.

* * * * *